(12) United States Patent
Sanders

(10) Patent No.: US 9,522,862 B2
(45) Date of Patent: Dec. 20, 2016

(54) SIMULATED MOVING BED SEPARATORS AND METHODS FOR ISOLATING A DESIRED COMPONENT

(71) Applicant: UOP LLC, Des Plaines, IL (US)

(72) Inventor: Robert Edward Sanders, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 297 days.

(21) Appl. No.: 14/319,548

(22) Filed: Jun. 30, 2014

(65) Prior Publication Data
US 2015/0376093 A1 Dec. 31, 2015

(51) Int. Cl.
C07C 7/12 (2006.01)
C07C 7/13 (2006.01)

(52) U.S. Cl.
CPC ............................. *C07C 7/13* (2013.01)

(58) Field of Classification Search
CPC ....................................................... C07C 7/12
USPC ................................. 585/822, 825, 826, 828
See application file for complete search history.

(56) References Cited

U.S. PATENT DOCUMENTS

| | | | |
|---|---|---|---|
| 3,636,180 A | 1/1972 | Broughton | |
| 5,750,820 A | 5/1998 | Wei | |
| 5,884,777 A | 3/1999 | Pan et al. | |
| 7,649,124 B2 | 1/2010 | Lee et al. | |
| 8,569,564 B2 | 10/2013 | Porter et al. | |
| 2005/0269268 A1* | 12/2005 | Hotier | B01D 53/0423 210/659 |
| 2013/0153500 A1 | 6/2013 | Frey et al. | |
| 2013/0331633 A1 | 12/2013 | Go et al. | |

FOREIGN PATENT DOCUMENTS

KR 929115 B1 11/2009

OTHER PUBLICATIONS

Sutano et al., Bed-Line Flushing and Optimization in Simulated Moving-Bed Recovery of Para-Xylene, Separation and Purification Technology, v 96, p. 168-181, Aug. 21, 2012; ISSN: 13835866; DOI: 10.1016/j.sepur.2012.05.031; Publisher: Elsevier.

* cited by examiner

*Primary Examiner* — Thuan D Dang

(57) ABSTRACT

A simulated moving bed separator and methods for isolating a desired component are provided. A method includes removing an extract from an extract bed of the simulated moving bed separator, where the extract includes the desired component, and where the simulated moving bed separator includes a plurality of adsorbent beds circularly coupled together. The simulated moving bed separator also includes a distributor and a plurality of conduits fluidly coupling the distributor to the adsorbent beds. The adsorbent beds include the extract bed and a secondary flush bed downstream from the extract bed. A secondary flush conduit is flushed with a secondary flush fluid while removing extract from the extract bed, where the secondary flush conduit fluidly couples the secondary flush bed with the distributor. The flush fluid includes the extract.

6 Claims, 4 Drawing Sheets

SIMULATED MOVING BED SEPARATORS AND METHODS FOR ISOLATING A DESIRED COMPONENT

TECHNICAL FIELD

The present disclosure generally relates to methods and apparatuses for isolating a desired component from a mixed feed, and more particularly relates to methods and simulated moving bed separators for isolating a desired component from a mixed feed using selective adsorption.

BACKGROUND

Selective adsorption can separate a desired component from a feed mixture by adsorbing the desired component while letting other components in the mixture flow by. The other components are referred to herein as "undesired components" to differentiate them from the desired component, but the undesired components may be used for other purposes or processes and therefore be desirable in their own right. An adsorption separator may use an adsorbent that has a higher affinity for the desired component than for the undesired components in the mixture, so the desired component is adsorbed on the surface and within pores, cavities, or other areas of the adsorbent. The adsorbent may adsorb some of the desired component, the undesired components, and other compounds, but the more preferred compounds are adsorbed more readily. Selective adsorption can also proceed by adsorbing undesired components and allowing the desired component to flow through the adsorbent for collection. In this description, the desired component is adsorbed by the adsorbent, but this description is also applicable to embodiments where the undesired components are adsorbed and the desired component flows through the adsorbent.

As the mixture flows over the adsorbent, the desired component is adsorbed so the fluid passing through the adsorbent has a lower concentration of the desired component, and therefore a higher concentration of other components. This adsorption process diminishes after a period of time because the available adsorption sites on the adsorbent are taken up. The undesired components in the mixture may then be drained or displaced from the adsorbent in a purification process. Additional fluid flowing through the adsorption bed pushes the undesired components out. A desorbent may then be introduced into the adsorbent bed, where the adsorbent preferentially adsorbs the desorbent over the desired component. The desorbent displaces the desired component from the adsorbent in a desorption process, and the desired component can then be collected with some excess desorbent.

A moving bed adsorption separator uses a plurality of adsorption beds filled with adsorbent, and the adsorption beds are passed through different "zones" for different process steps. For example, a first zone may introduce the mixed feed to the adsorption bed to remove the desired component, and a second zone may be a purification zone where the undesired components are removed in a raffinate. A desorption zone may follow the purification zone, where the desired component is desorbed and recovered. In a simulated moving bed separator using an adsorbent, a plurality of adsorption beds are fluidly connected together and fixed in position. Some simulated moving bed separators use a plurality of adsorption beds fluidly coupled in a circular manner, so fluids flow through the adsorption beds in a loop. i.e., fluid flows from the first adsorption bed into the second adsorption bed, fluid flows from the second adsorption bed into the third adsorption bed, and so on, and fluid from the last adsorption bed flows into the first adsorption bed. The adsorption beds pass through the various zones by changing or shifting feed and take-off locations from one adsorption bed to the next, where the relative position of the feed and take-off locations determine the zone each adsorption bed is in. For example, a plurality of conduits fluidly couple the adsorption beds to a distributor, and the distributor shifts or changes the feed bed, or the adsorption bed where the feed stream is introduced to the adsorption beds. The distributor changes the feed bed from one adsorption bed to an adjacent adsorption bed, and also changes other feeds and extractions from the adsorption beds. After a period of time, the distributor changes the feed bed again, such that each adsorption bed serves as the feed bed in turn.

The desired component is removed from the simulated moving bed separator in an extract, where the desorbent is fed into the adsorption beds to displace the desired component, as described above. The extract includes the desired component and the desorbent, which can be separated by distillation. The distributor changes the conduit used to remove the extract, and that conduit is rinsed before use to increase the purity of the recovered product. The conduit is typically rinsed with the desorbent because the desorbent will be present in the extract and the distillation system is in place to separate the desorbent from the desired component. However, energy is required to separate the desorbent and the desired component by distillation. The higher the concentration of desorbent, the more energy that is needed for the distillation.

Accordingly, it is desirable to develop methods and apparatus to separate a desired component from a mixture with a simulated moving bed separator that produces an extract with a higher concentration of desired product than when the extract conduit is rinsed with a desorbent. In addition, it is desirable to reduce the total amount of energy needed to recover the desired product than when the extract conduit is rinsed with a desorbent. Furthermore, other desirable features and characteristics of the present embodiment will become apparent from the subsequent detailed description and the appended claims, taken in conjunction with the accompanying drawings and this background.

BRIEF SUMMARY

Simulated moving bed separators and methods for isolating a desired component from a mixed feed are provided. In an exemplary embodiment, a method includes removing an extract from an extract bed of the simulated moving bed separator, where the extract includes the desired component, and where the simulated moving bed separator includes a plurality of adsorbent beds circularly coupled together. The simulated moving bed separator also includes a distributor and a plurality of conduits fluidly coupling the distributor to the adsorbent beds. The adsorbent beds include the extract bed and a secondary flush bed downstream from the extract bed. A secondary flush conduit is flushed with a secondary flush fluid while removing extract from the extract bed, where the secondary flush conduit fluidly couples the secondary flush bed with the distributor. The flush fluid includes the extract.

In accordance with another exemplary embodiment, a method for separating a desired component from a mixed fee stream includes introducing the mixed feed into a feed bed of a simulated moving bed separator, where the mixed feed includes the desired component and an undesired component. The simulated moving bed separator includes a plurality of adsorbent beds fluidly coupled together in a circular manner, a distributor, and a plurality of conduits fluidly coupling the distributor to the adsorbent beds. A raffinate is removed from a raffinate bed, where the raffinate includes the undesired components. A desorbent is introduced to a desorbent bed, and an extract is removed from an extract bed, where the extract includes the desired component and the desorbent. A secondary flush conduit is flushed with a flush fluid that is about 1 mass percent or more desorbent and about 80 mass percent or more desired component. The secondary flush conduit fluidly couples the distributor with the adsorbent bed downstream from the extract bed.

In accordance with a further exemplary embodiment, simulated moving bed separator includes a plurality of adsorbent beds fluidly coupled together in a circular manner, where the adsorbent beds include a raffinate bed, a desorbent bed, a feed bed, an extract bed, and a secondary flush bed. The simulated moving bed separator also includes a distributor and a plurality of conduits fluidly coupling the adsorbent beds to the distributor. The conduits include a raffinate conduit fluidly coupled to the distributor and to the raffinate bed, a desorbent conduit fluidly coupled to the distributor and to the desorbent bed, a feed conduit fluidly coupled to the distributor and to the feed bed, an extract conduit fluidly coupled to the distributor and to the extract bed, and a secondary flush conduit fluidly coupled to the distributor and to the secondary flush bed. The extract bed is configured to produce an extract, and the distributor is configured to introduce the extract into the secondary flush conduit.

BRIEF DESCRIPTION OF THE DRAWINGS

Various embodiments will hereinafter be described in conjunction with the following drawing figures, wherein like numerals denote like elements, and wherein:

FIG. 3A is before a valve step, and FIG. 3B is after the valve step; FIG. 4A is before a valve step, and FIG. 4B is after the valve step.

DETAILED DESCRIPTION

The following detailed description is merely exemplary in nature and is not intended to limit the application and uses of the embodiment described. Furthermore, there is no intention to be bound by any theory presented in the preceding background or the following detailed description.

The various embodiments described herein relate to methods and apparatuses for isolating a desired component from a mixed feed stream. Simulated moving bed separators are known in the industry, such as the simulated moving bed separator known by the trademark SORBEX® available from UOP, LLC of 25 East Algonquin Road, Des Plaines, Ill. 60016 U.S.A. A simulated moving bed separator includes a plurality of adsorbent beds, where a mixed feed is introduced to one of the adsorbent beds referred to as a feed bed, desorbent is introduced to an adsorbent bed referred to as a desorbent bed, extract with the desired component and desorbent is withdrawn from an extract bed, and raffinate with the undesired components is withdrawn from a raffinate bed. A plurality of conduits fluidly couples the adsorbent beds with a distributor that controls the flows to and from the various adsorbent beds. The adsorbent beds used to introduce and withdraw material are periodically changed in a rotational manner, where the distributor changes the flows to the appropriate conduits. When the adsorbent bed change is made, a first extract bed will change to a second extract bed, where the second extract bed is downstream from the first extract bed. Before the change, the conduit to the second extract bed is flushed to eliminate or reduce possible contaminants in the conduit that could be incorporated into the extract. The conduit to the second extract bed is flushed with a flush fluid that includes the extract, and the extract includes the desired component and the desorbent as described above. The flush fluid is carried with, and incorporated into, the extract. The total concentration of desorbent in the extract is reduced by flushing the conduit with extract instead of with desorbent, because the extract has a lower concentration of desorbent than the essentially pure desorbent that may otherwise be used for the flush. Separating the desorbent from the desired component by distillation requires less energy if there is less desorbent to be separated.

Figure 1:
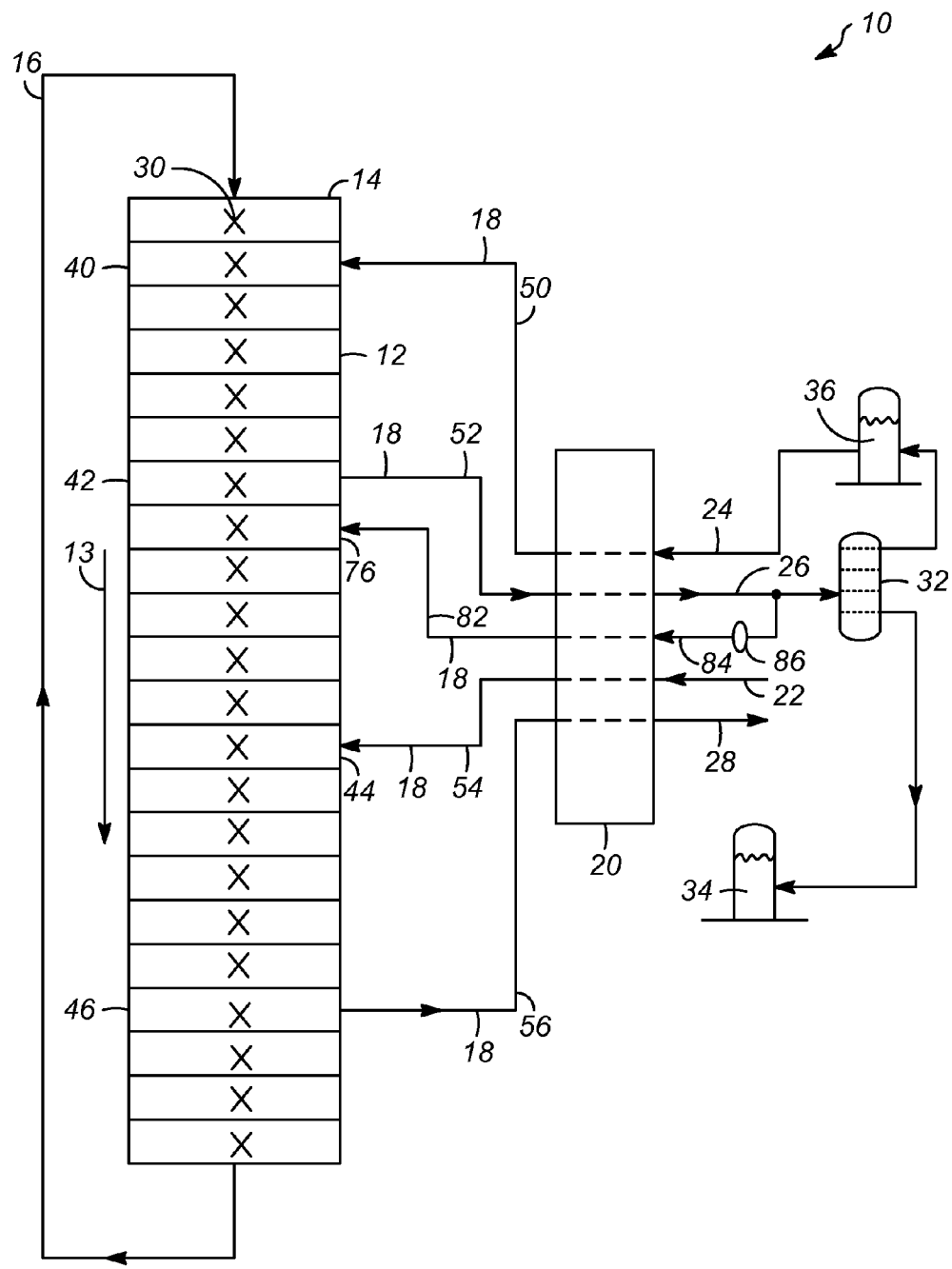
FIG. 1 is a schematic diagram of an exemplary embodiment of a simulated moving bed separator, where only the conduits for the mixed feed, desorbent, raffinate, extract, and secondary flush are illustrated.

Referring to an exemplary embodiment in FIG. 1, a simulated moving bed separator 10 includes a plurality of adsorbent beds 12 fluidly coupled together in a circular manner. Each adsorbent bed 12 receives fluid from the adsorbent bed 12 directly upstream from it, and each adsorbent bed 12 transfers fluid to the adsorbent bed 12 directly downstream from it. The direction of fluid flow through the adsorbent beds 12 is represented by arrow 13. Therefore, each adsorbent bed 12 is directly coupled to two other adsorbent beds 12, the one directly upstream from it and the one directly downstream from it. The adsorbent beds 12 may be connected in one continuous stack 14, as illustrated in FIG. 1, with a recirculation line 16 transporting fluid from the adsorbent bed 12 at the bottom of the stack 14 to the adsorbent bed 12 at the top of the stack 14, or from the adsorbent bed 12 at the top of the stack 14 to the adsorbent bed 12 at the bottom of the stack 14 in embodiments with upwards flow. The fluid flows through the adsorbent beds 12 in the stack 14, and is then recirculated from the last adsorbent bed 12 to the first adsorbent bed 12 by the recirculation line 16, so the flow is circular. In alternate embodiments, the adsorbent beds 12 may be in two or more stacks 14 with two or more recirculation lines 16 configured to carry fluid through the adsorbent beds 12 in a loop, as illustrated in the exemplary embodiment in FIG. 2, to be discussed in more detail below. The stacks 14 may include one, two, or more adsorbent beds 12 in various embodiments, but the flow is circular regardless of the number of stacks 14 in the simulated moving bed separator 10.

Figure 2:
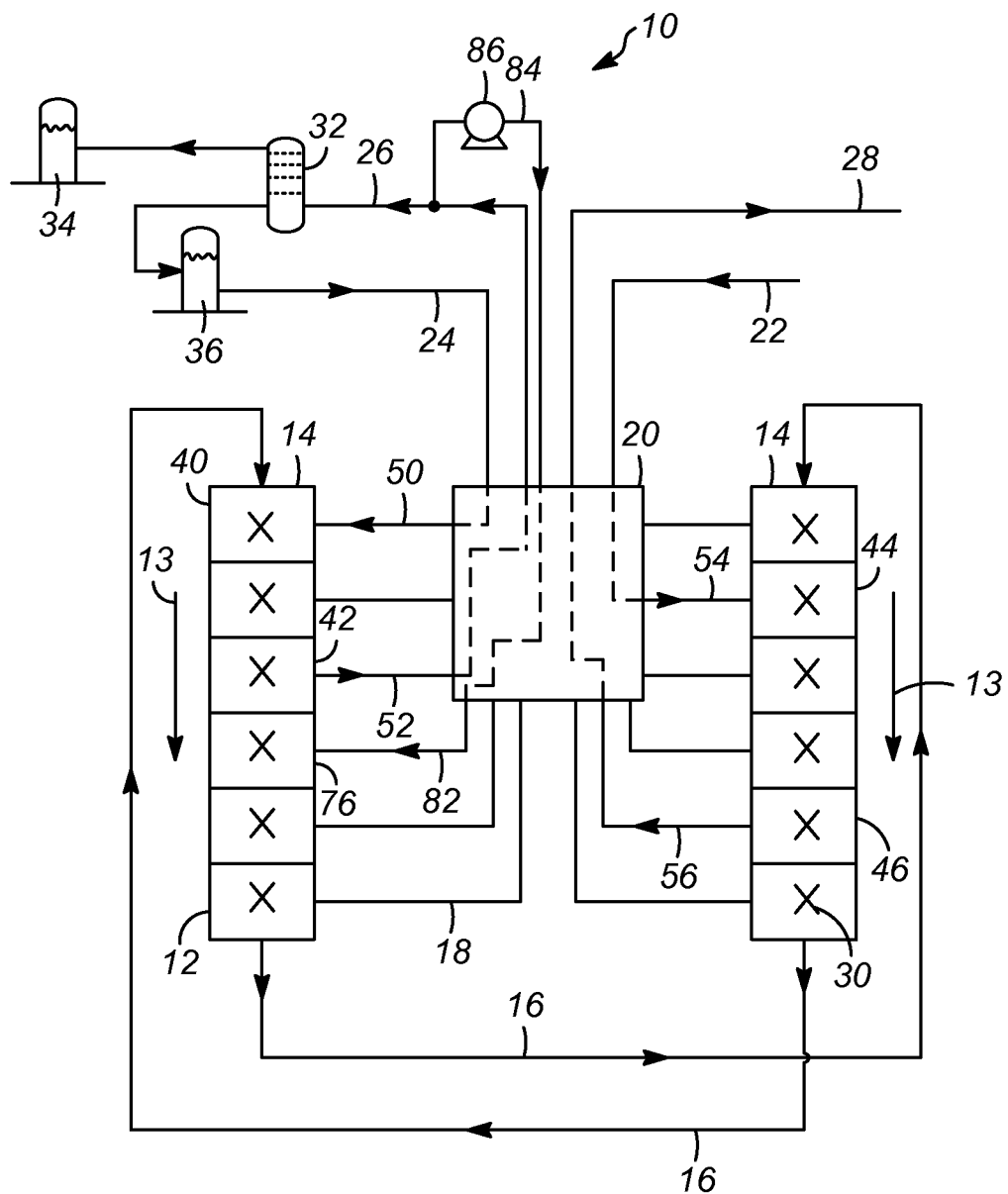
FIG. 2 is a schematic diagram of an alternate embodiment of a simulated moving bed separator with two stacks, where all the conduits are illustrated.

Referring to FIGS. 1 and 2, a plurality of conduits 18 fluidly couples the plurality of adsorbent beds 12 to a distributor 20. The distributor 20 moves the locations of the liquid input and output to the stack 14 by directing the appropriate fluid flow to the proper conduit 18, and therefore to the proper adsorbent bed 12. In some embodiments, the distributor 20 is a rotary valve, as is understood by those skilled in the art, but other types of distributors 20 can be used in alternate embodiments, such as a plurality of individual valves (not illustrated) that may be computer controlled. The conduits 18 have a volume, where the volume of the conduit 18 is the volume within the conduit 18 from the distributor 20 to the adsorbent bed 12. The distance between the distributor 20 and the various adsorbent beds 12 may vary from one adsorbent bed 12 to the next, so one or more of the conduits 18 may have a larger volume than others, and one or more conduits 18 will have the largest conduit volume. In some embodiments, the conduits 18 all have essentially the same diameter, so the conduit 18 with the longest length between the distributor 20 and the adsorbent bed 12 will have the largest volume. However, in other embodiments, the conduits 18 may have different diameters. If all the conduits 18 have the same volume, that volume is the largest volume for the conduits 18.

The distributor 20 directs fluid flow through the conduits 18 to the input and output locations, or adsorbent beds 12 used for the input or output of fluids. After a specified time period, which is called the step time in some embodiments, the distributor 20 advances one index and redirects the inputs and outputs to the adsorbent bed 12 directly downstream from the one previously in use in what is called a valve step. When the adsorbent bed 12 used for an input or output has completed an entire loop it is called a valve cycle, so each adsorbent bed 12 is used for each input and each output in one valve cycle. In many embodiments, there are at least two input streams and two output streams employed in the procedure, including a mixed feed stream 22, a desorbent stream 24, an extract stream 26, and a raffinate stream 28. The locations at which the mixed feed stream 22 and the desorbent stream 24 enter the simulated moving bed separator 10 and the extract stream 26 and the raffinate stream 28 leave the simulated moving bed separator 10 are simultaneously shifted in the same direction by the distributor 20. Each shift in location of these input or output points delivers or removes liquid from a different adsorbent bed 12 within the simulated moving bed separator 10.

In many embodiments, the volume of the plurality of adsorbent beds 12 is about constant, such as within about 5% of an average adsorbent bed volume, and the step time for each valve step is also about constant. In alternate embodiments, the volume of the adsorbent beds 12 varies from one adsorbent bed 12 to the next, and the step time may vary during a valve cycle. In an exemplary embodiment with a constant step time, the step time is about 60 to about 90 seconds, but in other embodiments the step time is about 15 minutes to about an hour, and other step times are also possible.

The adsorbent beds 12 include an adsorbent 30, and the type of adsorbent 30 varies depending on the use of the simulated moving bed separator 10. In an exemplary embodiment, the simulated moving bed separator 10 is used to separate para-xylene as a desired component 34 from a mixed xylene stream, where the ortho- and meta-xylene are undesired components. The mixed xylene stream may include other compounds besides xylene, such as ethyl benzene. As mentioned above, ortho- and meta-xylene have many beneficial uses and are valuable, so the reference to ortho- and meta-xylene as undesirable components is merely to distinguish them from the desired component 34, and not to disparage the value of ortho- and meta-xylene. In embodiments where the desired component 34 is para-xylene, the adsorbent 30 may be a zeolitic material that preferentially adsorbs para-xylene over meta-xylene, ortho-xylene, and ethylbenzene. In another embodiment where the desired component 34 is meta-xylene, the adsorbent 30 is a zeolitic material that preferentially adsorbs meta-xylene over para-xylene, ortho-xylene, and ethylbenzene. In yet another embodiment, the simulated moving bed separator 10 is used to separate olefins from paraffins where the desired component 34 is olefins, and the adsorbent 30 is a zeolitic material that preferentially adsorbs olefins over paraffins. In still another embodiment, the simulated moving bed separator 10 is used to separate normal paraffins from branched paraffins where the desired component 34 is normal paraffins, and the adsorbent 30 is a zeolitic material that preferentially adsorbs normal paraffins over branched paraffins. Many other uses and adsorbents 30 are possible in various embodiments, such as the separation of pharmaceutical materials, enzymes or other biological materials, or a wide variety of compounds. In various embodiments, the adsorbent 30 is charcoal, silica gel, ion-exchange resins, or many other materials.

The extract stream 26 includes the extract, where the extract includes the desired component 34 and desorbent 36. In an exemplary embodiment, the extract is about 50 mass percent or more desorbent 36, and about 50 mass percent or less desired component 34, but in alternate embodiments the extract is about 20 to about 80 mass percent desorbent 36 and about 80 to about 20 mass percent desired component 34. The extract stream 26 is transferred to an extract distillation column 32 to separate the desired component 34 from the desorbent 36. The extract stream 26 may be stored, such as in a tank, drums, tote bins, or other containers (not illustrated) before distillation, but the extract stream 26 flows directly to the extract distillation column 32 in some embodiments. In an exemplary embodiment, the desired component 34 is para-xylene and the desorbent 36 is toluene, but in other embodiments the desorbent 36 can be diethyl benzene or other compounds. When the desorbent 36 is toluene, the desorbent 36 has a lower boiling point than the desired component 34, para-xylene, so the toluene is vaporized and lifted in the extract distillation column 32. Lifting the desorbent 36 requires energy, so the lower the concentration of toluene in the extract stream 26, the less energy required to recover a set quantity of the desired component 34. In embodiments where the desorbent 36 has a higher boiling point than the desired component 34, the desired component 34 is lifted in the extract distillation column 32, but the desorbent 36 is still heated and processed so higher concentrations of desorbent 36 still increase the energy required in the extract distillation column 32. The desorbent 36 is re-used in the simulated moving bed separator 10 in many embodiments, and the desired component 34 is removed from the system.

In an exemplary embodiment, the desorbent 36 from the desorbent stream 24 is introduced to the stack 14 in a desorbent bed 40, where the desorbent bed 40 is one of the adsorbent beds 12. The extract is removed from the stack 14 in an extract bed 42, where the extract bed 42 is one of the adsorbent beds 12 downstream from the desorbent bed 40. In an exemplary embodiment, only one extract stream 26 is removed from the stack 14 at a time, so all the extract being removed from the stack 14 at one time has essentially the same composition. In an alternate embodiment, there is only one feed bed 44 in the stack 14 at any one time, so all the mixed feed is added to the stack 14 in the same feed bed 44. In an alternate embodiment, there is only one mixed feed stream 22 introduced to the stack 14 at any one time. The mixed feed stream 22 is introduced to the stack 14 in a feed bed 44, where the feed bed 44 is downstream from the extract bed 42. Therefore, the extract bed 42 is between the desorbent bed 40 and the feed bed 44. The mixed feed stream 22 includes the mixed feed, where the mixed feed includes the desired component 34 and the undesired components. The raffinate is removed from a raffinate bed 46, where the raffinate bed 46 is an adsorbent bed 12 positioned downstream from the feed bed 44 and upstream from the desorbent bed 40. As such, the desorbent bed 40 is between the raffinate bed 46 and the extract bed 42, the extract bed 42 is between the desorbent bed 40 and the feed bed 44, the feed bed 44 is between the extract bed 42 and the raffinate bed 46, and the raffinate bed 46 is between the feed bed 44 and the desorbent bed 40. A desorbent conduit 50, an extract conduit 52, a feed conduit 54, and a raffinate conduit 56 are conduits 18 that fluidly couple the desorbent bed 40, the extract bed 42, the feed bed 44, and the raffinate bed 46, respectively, to the distributor 20. With each valve step, the desorbent conduit 50, the extract conduit 52, the feed conduit 54, and the raffinate conduit 56 change, where FIG. 1 illustrates the conduits 18 with fluid flow, and FIG. 2 illustrates all the conduits 18, including those without any fluid flow.

Figures 3A, 3B:
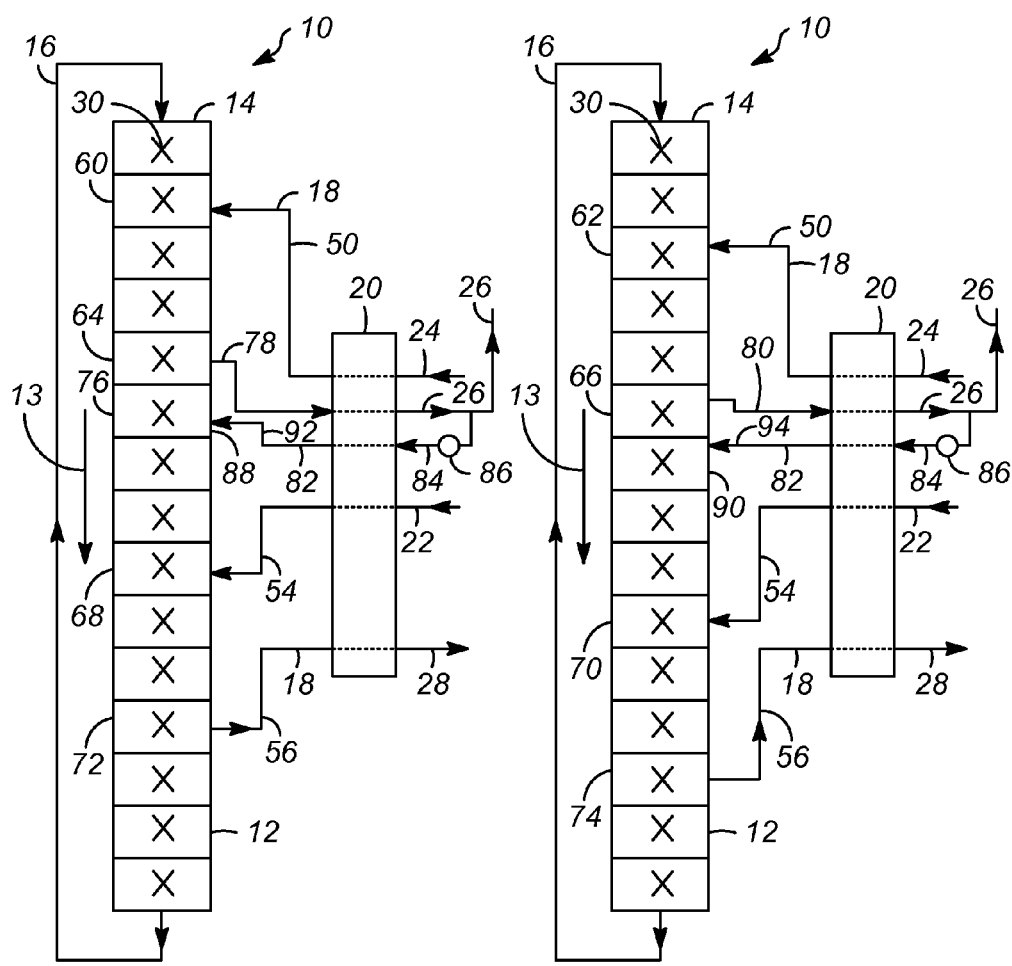
FIGS. 3A and 3B are schematic diagrams of an exemplary embodiment of a simulated moving bed separator, where

Referring to the exemplary embodiment illustrated in FIGS. 3A and 3B, the inputs and outputs to the stack 14 are shifted downstream to the adjacent adsorbent bed 12 in a valve step, where FIG. 3A illustrates the inputs and outputs before the valve step, and FIG. 3B illustrates the inputs and outputs after the valve step. Before the valve step, the desorbent bed 40 is a first desorbent bed 60, and after the valve step the desorbent bed 40 is a second desorbent bed 62, where the second desorbent bed 62 is directly downstream from the first desorbent bed 60. "Directly downstream" means the adjacent downstream adsorbent bed 12, so fluids flow directly from the upstream adsorbent bed 12 to the adjacent downstream adsorbent bed 12. In many embodiments, the second desorbent bed 62 is not used for introducing desorbent 36 into the stack 14 before the valve step, so before the valve step the second desorbent bed 62 is not one of the named desorbent bed 40, extract bed 42, feed bed 44, or raffinate bed 46. In the same manner, first desorbent bed 60 is not used for introducing desorbent 36 into the stack 14 after the valve step, so the first desorbent bed 60 reverts to simply one desorbent bed 40 in the stack 14 after the valve step. Therefore, each desorbent bed 40 will be a first desorbent bed 60 and a second desorbent bed 62 during one valve cycle, or complete loop of the stack 14, as mentioned above. In the same manner as for the desorbent bed 40 described above, the extract bed 42 is a first extract bed 64 before the valve step and a second extract bed 66 after the valve step; the feed bed 44 is a first feed bed 68 before the valve step and a second feed bed 70 after the valve step; and the raffinate bed 46 is a first raffinate bed 72 before the valve step and a second raffinate bed 74 after the valve step.

Figures 4A, 4B:
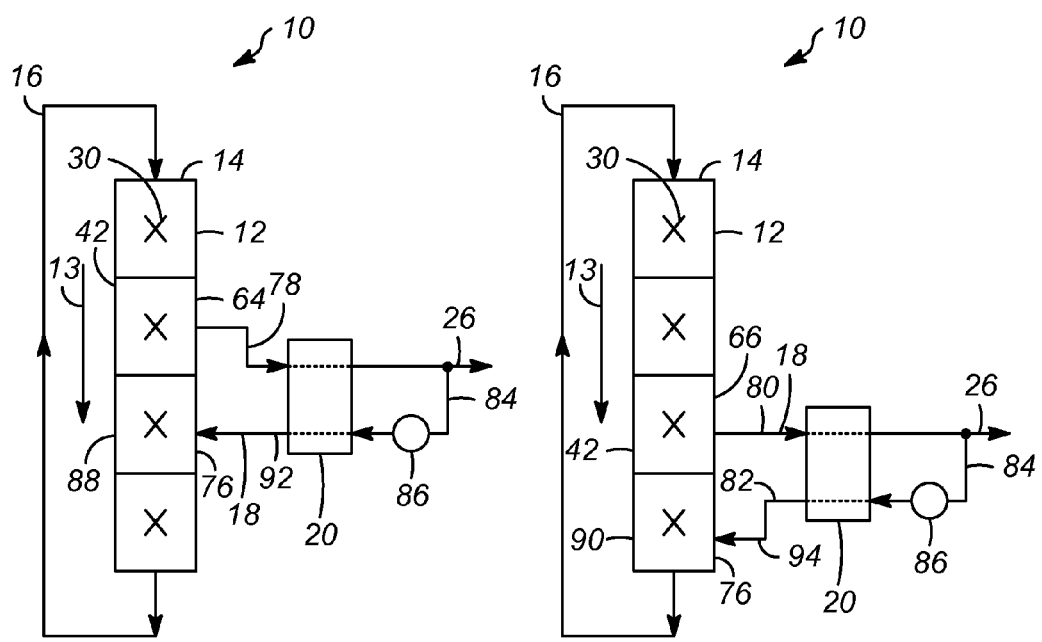
FIGS. 4A and 4B are schematic diagrams of the extract and secondary flush portion of a simulated moving bed separator, where

The exemplary embodiment in FIGS. 4A and 4B illustrate the portion of the stack 14 that includes the extract bed 42 and a secondary flush bed 76 directly downstream from the extract bed 42, but does not include the desorbent bed 40, the feed bed 44, or the raffinate bed 46 illustrated in FIGS. 3A and 3B. The secondary flush bed 76 is a first secondary flush bed 88 before the valve step, and a second secondary flush bed 90 after the valve step, and a secondary flush conduit 82 is a first secondary flush conduit 92 before the valve step and a second secondary flush conduit 94 after the valve step, as described above. FIG. 4A illustrates an embodiment before a valve step, and FIG. 4B illustrates the same embodiment after the valve step. In alternate embodiments (not illustrated), the secondary flush bed 76 is downstream from the extract bed 42, but the secondary flush bed 76 may not be directly downstream from the extract bed 42. For example, the secondary flush bed 76 may be downstream from the extract bed 42, where one or more intervening adsorbent beds 12 are positioned between the extract bed 42 and the secondary flush bed 76 so long as no fluids flow to or from the intervening adsorbent beds 12 through the associated conduits 18 and the distributor 20.

Reference is made to FIGS. 3A, 3B, 4A, and 4B. A first extract conduit 78 fluidly couples the first extract bed 64 to the distributor 20, and a second extract conduit 80 fluidly couples the second extract bed 66 to the distributor 20. The first secondary flush conduit 92 fluidly couples the first secondary flush bed 88 to the distributor 20, and the second secondary flush conduit 94 fluidly couples the second secondary flush bed 90 to the distributor 20. The first secondary flush bed 88 is the adsorbent bed 12 directly downstream from the first extract bed 64, and the second secondary flush bed 90 is the adsorbent bed 12 directly downstream from the second extract bed 66. Therefore, the first secondary flush conduit 92 before the valve step becomes the second extract conduit 80 when the valve step occurs, and the first secondary flush bed 88 before the valve step becomes the second extract bed 66 after the valve step.

To prevent or minimize contamination of the extract stream 26, the secondary flush conduit 82 is flushed with a secondary flush fluid from a secondary flush fluid stream 84, where the secondary flush fluid includes the extract. In an exemplary embodiment, the secondary flush fluid is about 99 mass percent or more extract, but the secondary flush fluid may be about 80 mass percent or more extract, or about 90 mass percent or more extract, or about 95 mass percent or more extract in alternate embodiments. In alternate embodiments, the flush fluid is about 50 mass percent or more desorbent 36, and about 50 mass percent or less desired component 34, or the flush fluid is about 20 to about 80 mass percent desorbent 36 and about 80 to about 20 mass percent desired component 34, where the desorbent 36 and desired component 34 may be from the extract or from other sources. The extract for the secondary flush fluid may be withdrawn from the extract stream 26 between the distributor 20 and the extract distillation column 32, as illustrated in exemplary embodiments in FIGS. 1 and 2 with continuing reference to FIGS. 3A, 3B, 4A, and 4B. An extract pump 86 may be used to pressurize the extract used in the secondary flush fluid. The extract may be pumped from the extract stream 26, or from a storage location for the extract.

In an exemplary embodiment, the secondary flush conduit 82 is flushed with a flush volume of the secondary flush fluid, where the flush volume is within about 5 volume percent of the volume of the conduit 18 with the largest volume. Each conduit 18 will serve as the secondary flush conduit 82 at some point within a valve cycle, so a single flush volume that is essentially equal to the largest conduit volume is adequate to flush the contents of the secondary flush conduit 82 prior to use as the extract conduit 52. In an alternate embodiment, the flush volume is within about 5 volume percent of the volume of the secondary flush conduit 82, so the flush volume may be varied for different conduits 18 that have different volumes. Any excess secondary flush fluid flows into the secondary flush bed 76, and is then withdrawn from the stack 14 with the extract after the subsequent valve step. The use of extract in the secondary flush fluid reduces the total concentration of desorbent 36 in the extract as compared to a similar secondary flush using desorbent 36. The simulated moving bed separator 10 may include other flushes of various conduits 18 in various embodiments (not illustrated), as is understood by those skilled in the art.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the application in any way. Rather, the foregoing detailed description will provide those skilled in the art with a convenient road map for implementing one or more embodiments, it being understood that various changes may be made in the function and arrangement of elements described in an exemplary embodiment without departing from the scope, as set forth in the appended claims.

What is claimed is:

1. A method of separating a desired component from a mixed feed stream, the method comprising the steps of:
    removing an extract from an extract bed of a simulated moving bed separator wherein the secondary flush bed is directly downstream from the extract bed, wherein the extract comprises the desired component, wherein the simulated moving bed separator comprises a plurality of adsorbent beds circularly coupled together, a distributor, and a plurality of conduits fluidly coupling the distributor to the plurality of adsorbent beds, and wherein the plurality of adsorbent beds comprises the extract bed and a secondary flush bed downstream from the extract bed;
    flushing a secondary flush conduit with a secondary flush fluid while removing extract from the extract bed, wherein the secondary flush conduit fluidly couples the secondary flush bed with the distributor, and wherein the secondary flush fluid comprises the extract;
    changing the extract bed from a first extract bed to a second extract bed in a valve step, wherein the second extract bed is the adsorbent bed directly downstream from the first extract bed such that the second extract bed is the same adsorbent bed as the secondary flush bed before the valve step;
    introducing the mixed feed into a feed bed, wherein the feed bed is downstream from the extract bed and wherein the mixed feed comprises the desired component and an undesired component;
    introducing a desorbent into a desorbent bed, wherein the extract comprises the desorbent and the desired component; and
    removing a raffinate from a raffinate bed, wherein the raffinate comprises the undesired component, and wherein the plurality of adsorbent beds comprise the feed bed, the desorbent bed and the raffinate bed, wherein the raffinate bed is downstream from the feed bed, the desorbent bed is downstream from the raffinate bed, and wherein removing the extract comprises removing the extract wherein the extract bed is downstream from the desorbent bed; wherein the desired component is para-xylene.

2. The method of claim 1 wherein removing the extract from the extract bed comprises removing the extract from the extract bed wherein the plurality of adsorbent beds comprise an adsorbent, and wherein the adsorbent is a zeolitic adsorbent that preferentially adsorbs para-xylene over meta-xylene, ortho-xylene, and ethylbenzene, and wherein the desired component is para-xylene.

3. The method of claim 1 further comprising:
    introducing the mixed feed stream into a feed bed, wherein the simulated moving bed separator comprises a single feed bed at any one time, and wherein the mixed feed stream comprises the desired component and an undesired component.

4. The method of claim 1 wherein flushing the secondary flush conduit comprises flushing the secondary flush conduit with the secondary flush fluid, wherein about 90 mass percent or more of the secondary flush fluid is the extract.

5. The method of claim 1 wherein flushing the secondary flush conduit comprises pumping extract to the distributor, and wherein the distributor directs the extract to the secondary flush conduit.

6. The method of claim 1 wherein flushing the secondary flush conduit with the secondary flush fluid comprises flushing the secondary flush conduit with a flush volume of the secondary flush fluid, wherein the flush volume is within about 5% of a largest conduit volume.

* * * * *